(12) United States Patent
Hegen

(10) Patent No.: US 8,715,225 B2
(45) Date of Patent: May 6, 2014

(54) BREAST PUMP

(75) Inventor: Marnix Hegen, Cambridge (GB)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/639,761

(22) PCT Filed: May 30, 2011

(86) PCT No.: PCT/IB2011/052361
§ 371 (c)(1),
(2), (4) Date: Oct. 5, 2012

(87) PCT Pub. No.: WO2011/154867
PCT Pub. Date: Dec. 15, 2011

(65) Prior Publication Data
US 2013/0072866 A1 Mar. 21, 2013

(30) Foreign Application Priority Data
Jun. 7, 2010 (EP) .................................. 10165038

(51) Int. Cl.
*A61M 1/06* (2006.01)
(52) U.S. Cl.
USPC ............ 604/73; 604/74; 604/75; 604/76; 119/14.01

(58) Field of Classification Search
USPC .................... 604/73–76; 119/14.01
See application file for complete search history.

(56) References Cited

U.S. PATENT DOCUMENTS

| | | | |
|---|---|---|---|
| 4,673,388 A * | 6/1987 | Schlensog et al. | 604/74 |
| 4,740,196 A | 4/1988 | Powell | |
| 2006/0247559 A1 | 11/2006 | Fei | |

FOREIGN PATENT DOCUMENTS

| | | |
|---|---|---|
| CN | 2453909 U | 10/2001 |
| CN | 1958084 A | 5/2007 |
| GB | 2155792 A | 10/1985 |
| JP | 07000504 A | 1/1995 |
| JP | 2007330702 A | 12/2007 |
| TW | 200950834 A | 12/2009 |
| WO | 200047247 A1 | 8/2000 |

\* cited by examiner

*Primary Examiner* — Jason Flick
*Assistant Examiner* — Scott Medway

(57) ABSTRACT

When milk is expressed using a breast pump, milk residue is left on a surface of a breast pump funnel (13). The present invention relates to a breast pump with a vibrating means (30) which is configured to induce the breast pump to vibrate to promote the flow of residual milk on a surface of the funnel (13) to flow to a milk collecting vessel (14). The invention also relates to a method of collecting milk residue on a surface of a funnel for a breast pump by vibrating the breast pump after milk has been expressed from a user's breast.

5 Claims, 7 Drawing Sheets ically driven vibrating element. The electrically driven
BREAST PUMP

FIELD OF THE INVENTION

The present invention relates to a breast pump. The present invention also relates to a method of collecting milk residue on a surface of a funnel for a breast pump.

BACKGROUND OF THE INVENTION

Breast pumps are well known devices for extracting milk from a breast of a user. A breast pump may be used if the baby or infant is not itself able to express milk from the breast, or if the mother is separated from the baby or infant, for example, if away from the baby at work. The use of a breast pump to express milk may also be used to stimulate and increase milk production in women with a low milk supply.

Breast pumps make use of a vacuum to induce milk expression from a nursing mother's breast. The pumping action of the device draws the milk from the nipple to a collection vessel, and the pressure and/or frequency may be adjusted to the preferences of the mother.

A known breast pump for extracting milk from a user's breast is shown in FIG. 1. Such a breast pump unit 1 comprises a main body 2 and a collection vessel 3, such as a feeding bottle or bag. The collection vessel 3 is attached to the main body 2 by a screw fitting.

A breast-receiving funnel 5 is fixedly attached to the main body 2 for receiving the breast of a user. The funnel 5 has an inner surface 6 and comprises a mouth 7 and a throat 8. The mouth 7 is open at an outer end and the inner surface of the funnel 5 converges from the outer end towards the throat 8 to form a hollow recess in which a breast is received.

A vacuum pump unit (not shown) is formed in the main body 2 to create a vacuum, and comprises a diaphragm mounted in the main body to generate the required vacuum at the breast for milk expression. The diaphragm is deformed by means of a user manually operating a handle 4 extending from the main body 2, by means of a small electric motor mounted to or in the main body, or by means of an attached vacuum tube connected to a desktop base containing an electric vacuum pump (not shown).

Expressed milk is considered to be very precious and is known to have a high emotional value to mothers that have expressed milk from their breasts. However, a problem with a breast pump, as described above, is that milk is known to adhere to an inner surface of the funnel and the main body, and so not all the expressed milk is delivered to the collection vessel for use. Therefore, this residual milk is considered to be a loss to a user, and this loss of milk may have an emotional impact on a mother.

SUMMARY OF THE INVENTION

The present invention seeks to overcome or substantially alleviate the aforementioned problems.

According to the present invention, there is provided a breast pump comprising a main body, a funnel, a vacuum pump unit to generate a vacuum and a vibrating means, wherein the vibrating means is configured to induce the main body and funnel to vibrate to promote the flow of residual milk on a surface of the funnel to flow to a milk collecting vessel, and wherein the vibrating means is configured to vibrate following operation of the vacuum pump unit to express milk.

The breast pump may further comprise a fluid passageway in the main body extending between the funnel and a milk collecting vessel, wherein the vibrating means is configured to vibrate the main body to promote the flow of residual milk in the fluid passageway to flow to a milk collecting vessel.

Advantageously, the vibrating means comprises first and second friction elements, the first friction element being configured to slide against the second friction element to induce the main body and funnel to vibrate.

Conveniently, the first friction element is a collar circumferentially extending around the main body or funnel.

In one embodiment, the vibrating means comprises an electrically driven vibrating element. The electrically driven vibrating element may be an unbalanced electric motor.

Conveniently, the vacuum pump unit comprises a pump motor.

Preferably, the vibrating means comprises an electromagnet which is operable to act on a drive shaft of the pump motor to unbalance the pump motor when the electromagnet is operated so that the pump motor is induced to vibrate. Advantageously, the vibrating means is actuated by a switch. The switch may be configured to alternately actuate the vibrating means or the vacuum pump unit.

The breast pump may further comprise a control unit configured to actuate the vibrating means to induce the main body or funnel to vibrate following operation of the vacuum pump unit to express milk.

In one embodiment, the control unit is configured to operate the vibrating means after the vacuum pump unit has been operated for a predetermined length of time.

In another embodiment, the control unit is configured to operate the vibrating means in response to a signal that the vacuum pump unit has stopped.

According to the invention, milk residue on a surface of a funnel for a breast pump is collected, wherein the breast pump is operated to stimulate milk expression from a user's breast, and wherein the breast pump is subsequently vibrated to promote the flow of residual milk on a surface of the funnel to flow to a milk collecting vessel.

These and other aspects of the invention will be apparent from and elucidated with reference to the embodiments described hereinafter.

BRIEF DESCRIPTION OF THE DRAWINGS

Preferred embodiments will now be described, by way of example only, with reference to the accompanying drawings, in which.

DETAILED DESCRIPTION OF THE EMBODIMENTS

Figure 1:
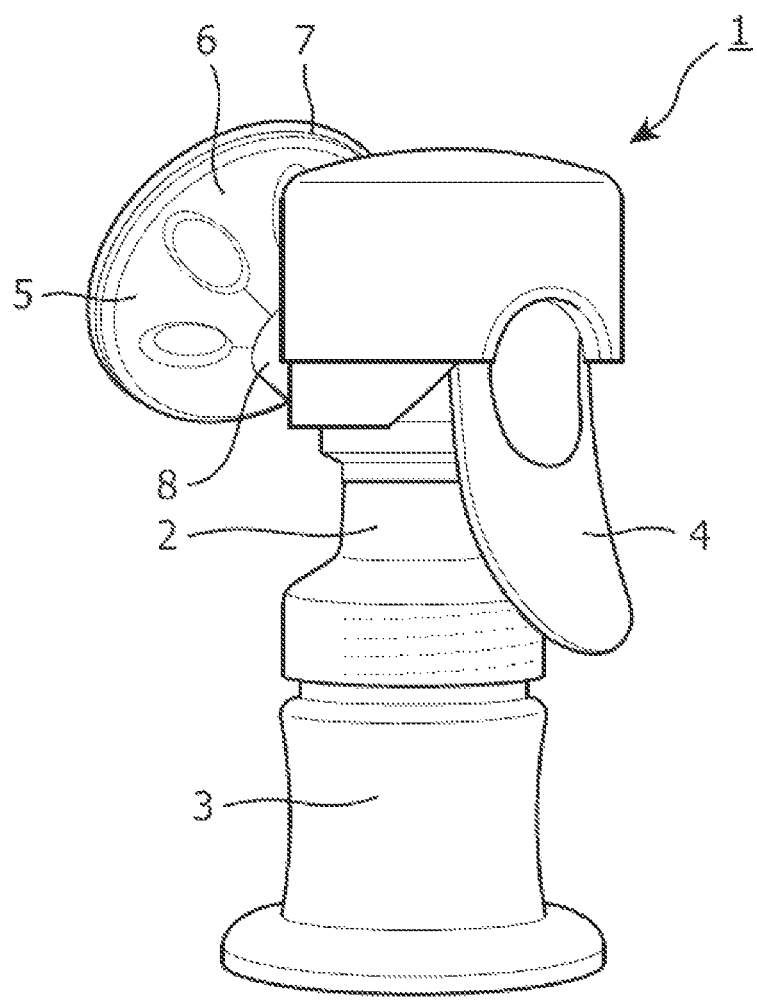
FIG. 1 shows a perspective view of an existing breast pump.

FIG. 1 represents a reference view of a breast pump and has already been described above.

Figure 2:
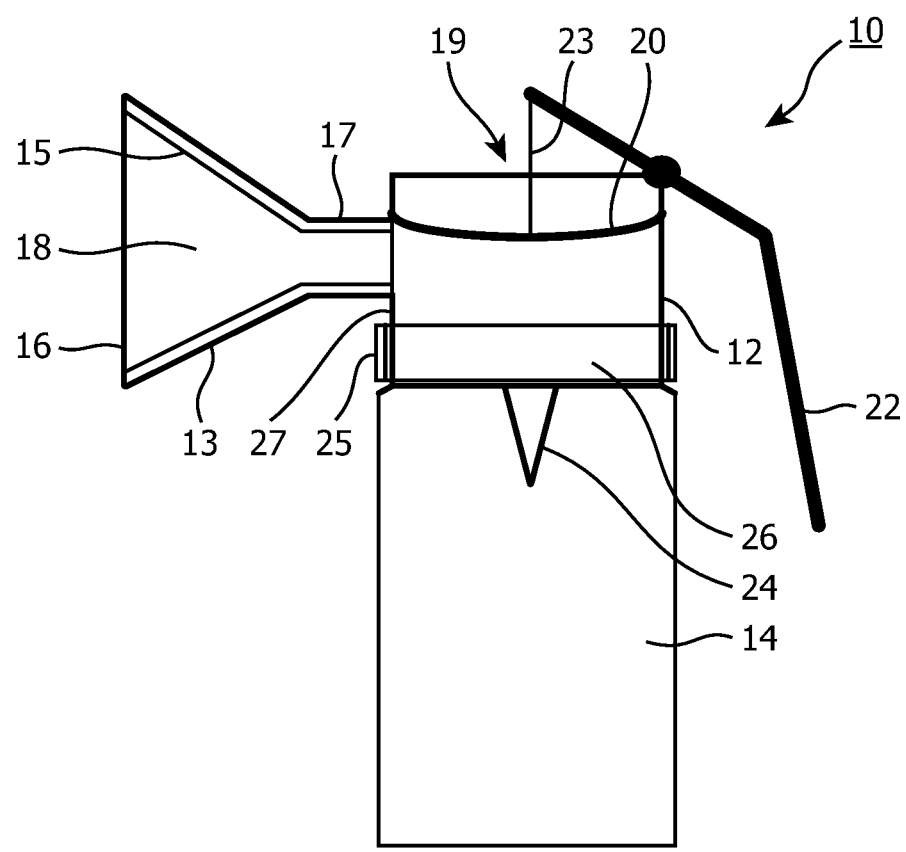
FIG. 2 shows a schematic cross-sectional of a breast pump according to a first embodiment.

Referring now to FIG. 2, a breast pump 10 is shown comprising a main body 12, a funnel 13 and a milk-receiving vessel 14. The milk receiving vessel 14 is a feeding bottle for an infant or baby; however it will be appreciated that the vessel 14 may alternatively be a bag or other known container.

The funnel 13 has an inner surface 15 extending between a mouth 16 and a throat 17 of the funnel 13. The mouth 16 is open at an outer end and converges toward the throat 17 to form a breast receiving recess 18. The throat 17 of the funnel 13 extends from the main body 12 such that a fluid passageway is formed from the breast receiving recess 18, through the main body 12 to the milk receiving vessel 14.

A vacuum pump unit 19 is disposed in the main body 12 to create a vacuum in the main body 12 and breast receiving recess 18 of the funnel 13. The vacuum pump unit 19 comprises a diaphragm 20 and a handle 22. The handle 22 is pivotally mounted to the main body 12 and is fixedly mounted to the diaphragm 20 by a connecting member 23 so that the handle is manually operable to deform the diaphragm and therefore operate the vacuum pump unit 19, as will become apparent hereinafter. The vacuum pump unit 19 is conventional and so no further description of the pump unit will be given herein. Alternatively, the vacuum pump unit 19 is motorized, and comprises an electric motor (not shown) which fixedly mounts to the connecting member 23 to cyclically deform the diaphragm 20 and therefore create a vacuum. The motor may be disposed in the main body 12, or in a motor unit (not shown) mounted to the main body 12.

A valve 24 is disposed along the fluid passageway between the vacuum pump unit 19 and the milk receiving vessel 14 in order to seal the breast receiving recess 18 from the atmospheric pressure in the receiving vessel 14 when the diaphragm 20 starts to deform.

A vibrating means 25 is mounted to the main body 12 of the pump 10. The vibrating means 25 comprises a circumferentially extending collar 26 which extends around a cylindrical portion 27 of the main body 12. An inner face of the collar 26 locates against an outer face of the cylindrical portion 27 of the main body 12 such that the collar 26 is rotatable about the cylindrical portion 27.

The inner face of the collar 26 has a rough surface which lays against a corresponding rough surface of the outer face of the main body cylindrical portion 27 such that peaks of one of the rough surfaces locate against and interact with opposing peaks on the other rough surface. The collar 26 is configured to circumferentially rotate about the main body 12 so that the opposing surfaces of the inner face of the collar and outer face of the main body cylindrical portion slide against each other. Therefore, the rough surfaces are urged to slide against each other such that peaks of the rough surfaces are urged to contact and slide relative to opposing peaks and troughs to induce vibration in the main body 12.

Alternatively, it is envisaged that the inner face of the collar 26 comprises upstanding protrusions (not shown) which abut against corresponding protrusions (not shown) upstanding from the outer face of the main body cylindrical portion 27. Therefore, when a user rotates the collar 26 relative to the main body 12, the protrusions act against each other and move relative to each other. This movement of protrusions over each other induces the main body 12 to vibrate. The protrusions may have different forms, for example conical, cylindrical, ridges or bumps. The protrusions may be resilient to increase vibration and to reduce protrusion wear.

Operation of the first embodiment of a breast pump will now be described. A user inserts a breast (not shown) into the breast receiving recess 18 formed by the funnel 13 and locates the breast against the inner surface 15 of the funnel 13 to form an air-tight seal. The user then operates the vacuum pump unit 19 by repeatedly pressing the handle 22 to cyclically deform the diaphragm 20 and therefore create a vacuum in the breast receiving recess 18 and main body 12 so that milk is expressed from the user's nipple and flows from the breast receiving recess 18 along the fluid passageway defined by the main body 12 to the milk receiving vessel 14. The user continues to operate the vacuum pump unit 19 until the desired quantity of milk has been expressed. The user then removes the breast pump 10 from the breast. However, milk residue is left on the inner surface 15 of the funnel 13 and along the fluid passageway defined in the main body 12.

To urge the milk residue to flow to the milk receiving vessel 14, a user holds the vacuum pump 10 and grasps the collar 26 of the vibrating means 25. The user then urges the collar 26 to circumferentially rotate around the main body 12 of the breast pump 10 so that the opposing surfaces of the inner face of the collar and outer face of the main body cylindrical portion are urged to slide relative to each other to induce vibration in the main body.

As the main body vibrates, the funnel is also induced to vibrate and so the milk residue is urged to flow from being adhered to the inner surface 15 of the funnel 13 and along the fluid passageway defined in the main body 12 to the milk collecting vessel 14. Therefore, loss of milk expressed from a user's breast will be minimized.

Although in the present embodiment the vibrating means 25 is a mechanically operated ring element, it will be appreciated that the vibration means may be any suitable mechanical arrangement for moving one surface relative to another so that the surfaces interact to induce a vibration of the breast pump 10.

Although in the present embodiment the vibrating means 25 is disposed on the main body 12, it will be appreciated that in an alternative arrangement the vibrating means 25 is disposed on another part of the breast pump 10, for example it is envisaged that a collar is disposed around the mouth 16 or throat 17 of the funnel 13, with an inner face of the collar locating against an outer face of the mouth 16 or throat 17. Alternatively, it is envisaged that a collar is disposed around the milk receiving vessel 14, with an inner face of the collar locating against an outer face of the milk receiving vessel 14.

Figure 3:
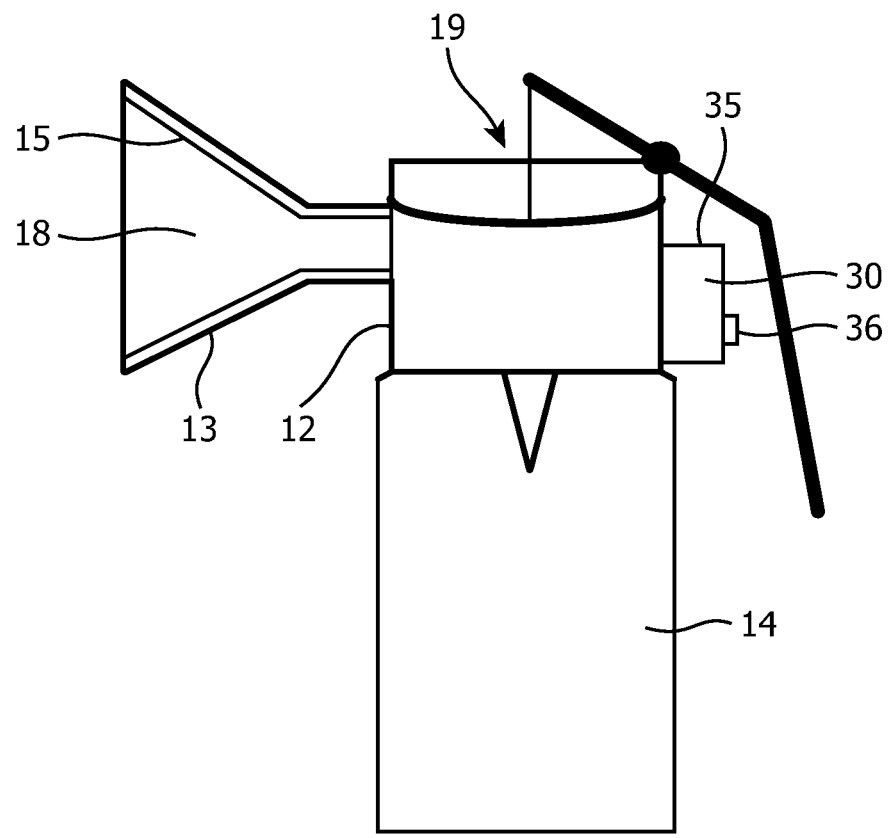
FIG. 3 shows a schematic cross-sectional of a breast pump according to a second embodiment.
Figure 4:
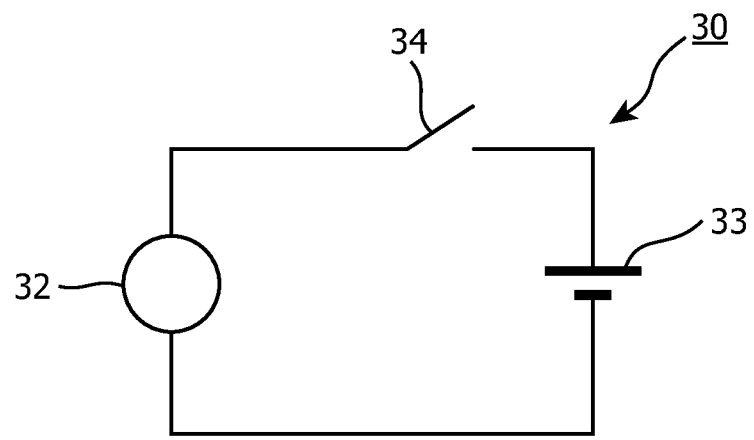
FIG. 4 shows an electrical diagram of the breast pump shown in FIG. 3.

Referring now to FIGS. 3 and 4, a second embodiment of a breast pump is shown. The breast pump shown in FIG. 3 has the same general arrangement and features as the breast pump shown in the first embodiment described above, and so a detailed description will be omitted herein. Furthermore, features and components corresponding to features and components described above will retain the same reference numerals.

The second embodiment of a breast pump has a vibrating means 30 mounted to the main body 12 of the breast pump 10. Referring to FIG. 4, the vibrating means 30 comprises an unevenly balanced electric motor 32, a power supply means 33 and a switch 34. The power supply means 33 in the present embodiment is a battery (not shown), although an external power supply unit may be used and connected to the electric motor by a wire (not shown).

The unevenly balanced electric motor 32 and battery are disposed in a housing 35 which is fixedly mounted to the main body 12. A push button 36, or other actuating means, is disposed on the housing 35 to actuate the switch 34 and activate the vibrating means 30. The housing 35 may be removed to access the battery and other components of the vibrating means 30.

The unevenly balanced electric motor 32 comprises a small electric motor with a rotatable shaft and a weight mounted to the motor shaft which is spaced from the longitudinal axis of the shaft so that the motor vibrates when operated.

Although in the present embodiment the vibrating means 30 is fixedly mounted to the main body 12, it will be appreciated that in an alternative embodiment the vibrating means 30 is mounted to the funnel 13 or the milk-receiving vessel 14. Alternatively, the vibrating means may be disposed in the main body 12.

In FIG. 3, a vacuum pump unit 19 is shown disposed in the main body 12 to create a vacuum in the main body 12 and breast receiving recess 18 of the funnel 13 and comprises the diaphragm 20 which is manually operated by the handle 22 to deform the diaphragm. However, it is also envisaged that the vacuum pump unit 19 may comprise an electric motor to cyclically deform the diaphragm 20 and create a vacuum.

Operation of the breast pump will now be described with reference to FIGS. 3 and 4. A user inserts a breast (not shown) into the breast receiving recess 18 formed by the funnel 13 and locates the breast against the inner surface 15 of the funnel 13 to form an air-tight seal. The user then operates the vacuum pump unit 19 so that milk is expressed from the user's nipple and flows from the breast receiving recess 18 along the fluid passageway defined by the main body 12 to the milk receiving vessel 14. The user continues to operate the vacuum pump unit 19 until the desired quantity of milk has been expressed. The user then removes the breast pump 10 from the breast. However, milk residue is left on the inner surface 15 of the funnel 13 and along the fluid passageway defined in the main body 12.

The user then presses the push button 36 to actuate the switch 33. This completes the electrical circuit and so the motor 32 vibrates. The main body 12 and funnel 13 are then urged to vibrate and so milk residue flows from being adhered to the inner surface 15 of the funnel 13 and along the fluid passageway defined in the main body 12 to the milk collecting vessel 14. Therefore, milk residue is guided to the milk receiving vessel and the loss of milk expressed from a user's breast will be minimized. The user then releases the push button 36 to stop the supply of power to the electric motor 32 and so the breast pump ceases to vibrate.

Figure 5:
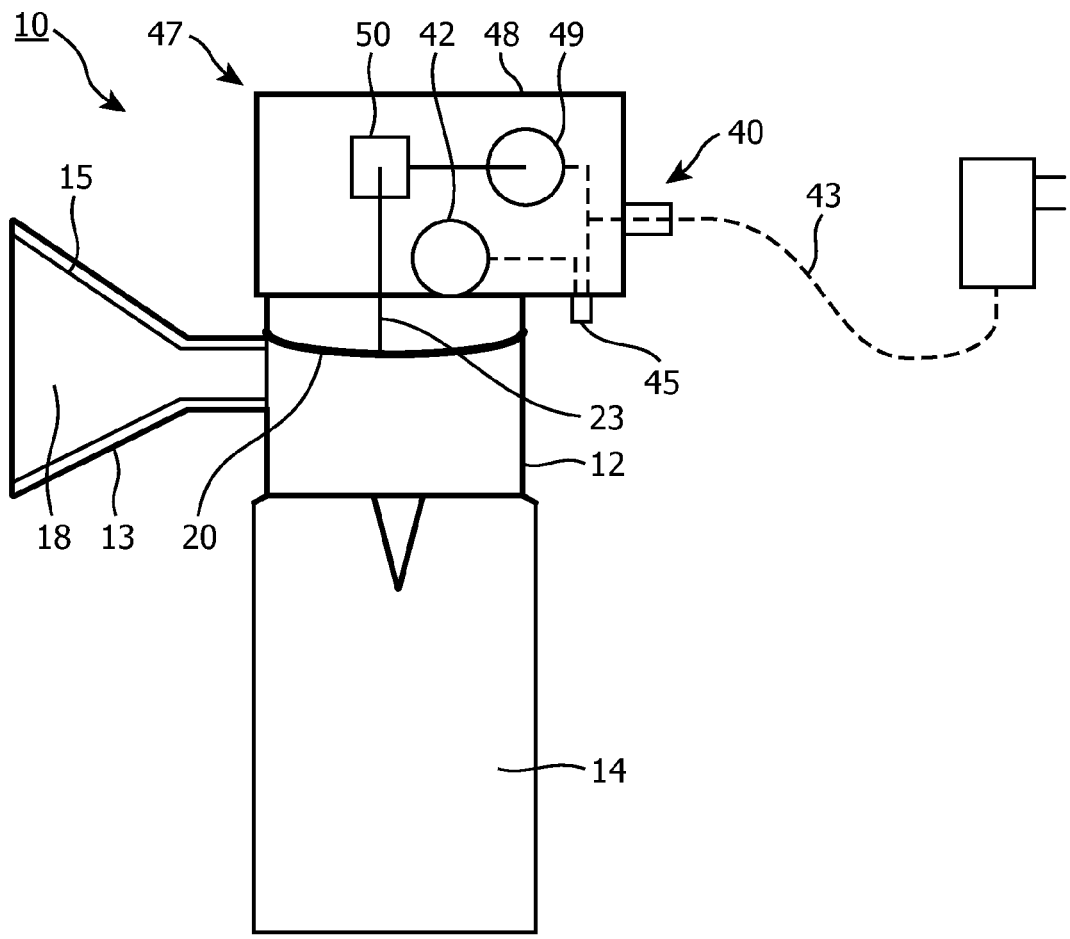
FIG. 5 shows a schematic cross-sectional of a breast pump according to a third embodiment.
Figure 6:
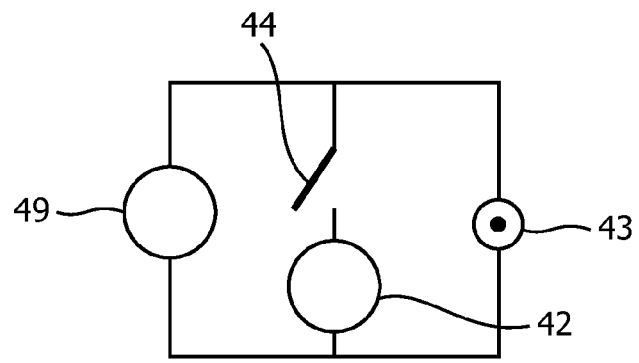
FIG. 6 shows an electrical diagram of the breast pump shown in FIG. 5.

Referring now to FIGS. 5 and 6, a third embodiment of a breast pump is shown. The breast pump shown in FIG. 5 has the same general arrangement and features as the breast pump shown in the second embodiment described above, and so a detailed description will be omitted herein. Furthermore, features and components corresponding to features and components described above will retain the same reference numerals.

In FIG. 5, a vacuum pump unit 47 is shown comprising the diaphragm 20 disposed in the main body 12 to create a vacuum in the main body 12 and breast receiving recess 18 of the funnel 13 and a motor unit 48 mounted to the main body 12 which is connected to the diaphragm 20 by the connecting element 23, and cyclically deforms the diaphragm 20. The motor unit 48 comprises a pump motor 49 and a gearbox 50. The gearbox 50 and connecting member 23 form a mechanical link between the pump motor 49 and the diaphragm 20, so that the pump motor 49 is operable to cyclically deform the diaphragm 20. A power supply means 43 is connected to the pump motor 49 to supply power the pump motor 49. The power supply means 43 in the present embodiment is an external power supply unit which is connected to the pump motor 49 by a wire, although it will be appreciated that a battery may be used which is disposed in the motor unit 48.

Referring to FIG. 6, a vibrating means 40 is disposed in the motor unit 48. The vibrating means 40 comprises an unevenly balanced electric motor 42 and a switch 44. A push button 45, or other actuating means, is disposed on the motor unit 48 to actuate the switch 44 and activate the vibrating means 40. The unevenly balanced electric motor 42 is electrically connected to the power supply means 43 by the switch 44. Alternatively, the vacuum pump unit and vibrating means may have independent power supply means.

Although in the present embodiment the vibrating means 40 is disposed in the motor unit 48, it will be appreciated that in an alternative arrangement the vibrating means 40 is mounted to the funnel 13 or the milk-receiving vessel 14. Alternatively, the vibrating means may be disposed in the main body 12.

Operation of the breast pump will now be described with reference to FIGS. 5 and 6. A user inserts a breast (not shown) into the breast receiving recess 18 formed by the funnel 13 and the vacuum pump unit 47 is then operated by supplying power to the pump motor 49 by the external power supply unit so that the diaphragm is cyclically deformed and milk is expressed from the user's nipple and flows from the breast receiving recess 18 along the fluid passageway defined by the main body 12 to the milk receiving vessel 14. When the desired quantity of milk has been expressed, the user removes the breast pump 10 from the breast. However, milk residue is left on the inner surface 15 of the funnel 13 and along the fluid passageway defined in the main body 12.

The user then presses the push button 45 to actuate the switch 44 and the motor 42 is operated so that the vibrating means vibrates. This induces the main body 12 and funnel 13 to vibrate and so milk residue is urged to flow from being adhered to the inner surface 15 of the funnel 13 and along the fluid passageway defined in the main body 12 to the milk collecting vessel 14. Therefore, residual milk is guided to the milk receiving vessel and so the loss of milk expressed from a user's breast will be minimized. The user then releases the push button 45, which stops the electric motor 42 and the breast pump ceases to vibrate.

Although in the present embodiment the pump motor operates constantly, it will be appreciated that in an alternative embodiment, the switch may be operable to actuate the pump motor. In such an arrangement, a single button may be operable to toggle between operation of the vacuum pump unit and the vibrating means. Alternatively, the vacuum pump may comprise separate switches operated by individual buttons to operate the vacuum pump and vibrating means independently.

Although in the above embodiment the pump motor 49 is operable to deform a diaphragm, it will be appreciated that the vacuum pump unit is not limited thereto, and that a pump motor may be used in an alternative arrangement to generate a vacuum in the breast receiving recess 18, for example in a compressor type arrangement with a pressure release valve.

Figure 7:
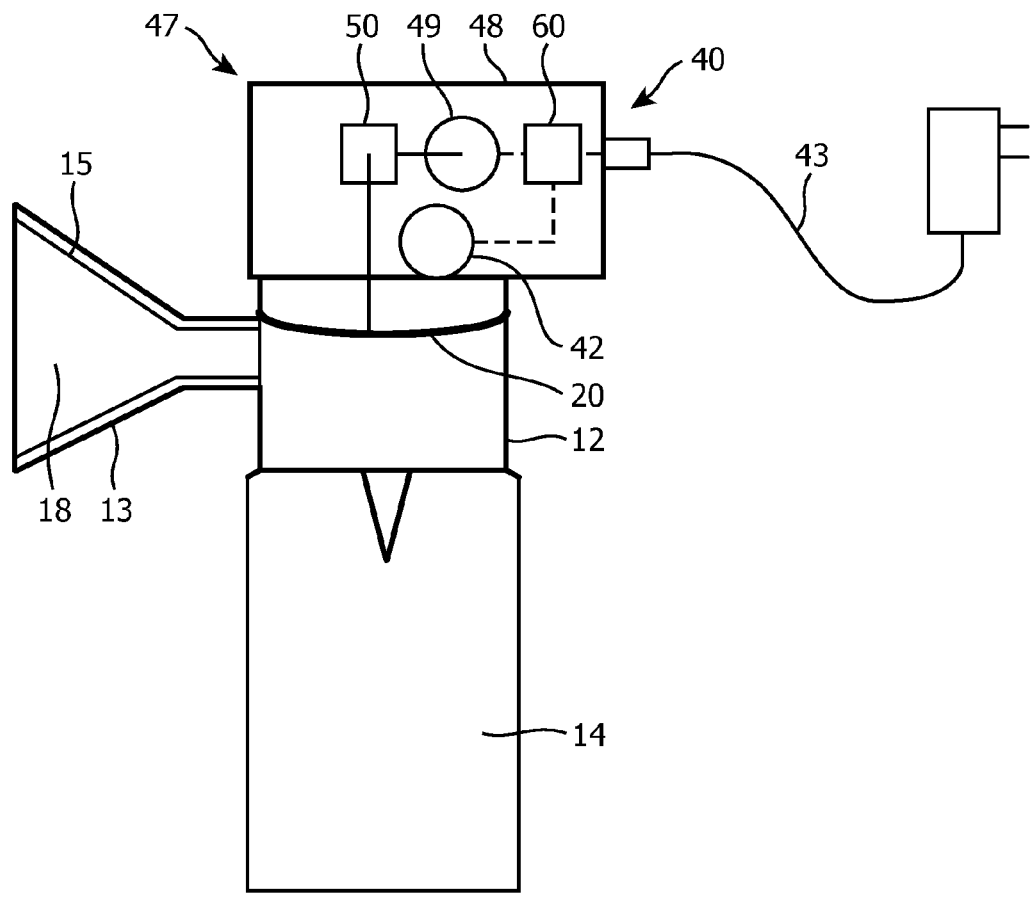
FIG. 7 shows a schematic cross-sectional of a breast pump according to a fourth embodiment.
Figure 8:
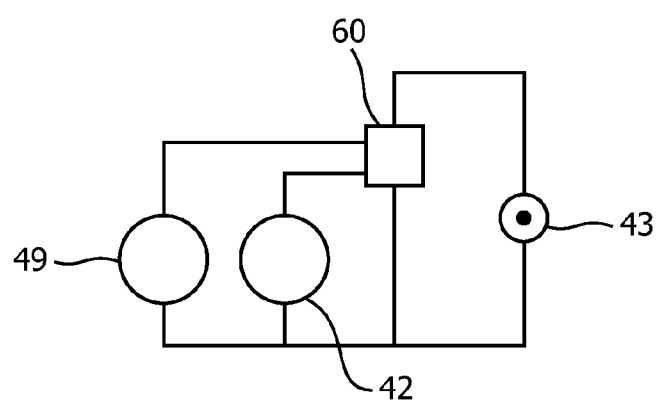
FIG. 8 shows an electrical diagram of the breast pump shown in FIG. 7.

Referring now to FIGS. 7 and 8, a fourth embodiment of a breast pump is shown. The breast pump shown in FIG. 7 has the same general arrangement and features as the third embodiment of the breast pump described above and shown in FIGS. 5 and 6, and so a detailed description will be omitted herein. Furthermore, features and components corresponding to features and components described above will retain the same reference numerals.

However, the fourth embodiment further comprises a control unit 60. The control unit 60 is disposed in the motor unit 48 and is configured to operate the vacuum pump unit 47 by supplying power to the pump motor 49, and to control the vibrating means 40 by supplying power to the unevenly balanced electric motor 42.

In the present embodiment, the control unit 60 is actuated by the supply of power from the external power supply unit, however it is envisaged that the control unit 60 may be actuated by a button (not shown) disposed on the motor unit 48, or elsewhere on the breast pump.

Operation of the breast pump will now be described with reference to FIGS. 7 and 8. A user inserts a breast (not shown) into the breast receiving recess 18 formed by the funnel 13 and the user supplies power to the breast pump by connecting the external power supply unit. Alternatively, the user operates a switch to supply power from a battery mounted to, or disposed in the motor unit 48. The control unit 60 operates the vacuum pump unit 47 so that the pump motor 49 is actuated and the diaphragm 20 is cyclically deformed. Therefore, milk is expressed from the user's nipple and flows from the breast receiving recess 18 along the fluid passageway defined by the main body 12 to the milk receiving vessel 14. When the desired quantity of milk has been expressed, the user removes the breast pump 10 from the breast. However, milk residue is left on the inner surface 15 of the funnel 13 and along the fluid passageway defined in the main body 12.

The control unit 60 then actuates the vibrating means 40 by actuating the electric motor 42 so that the main body 12 and funnel 13 are induced to vibrate, and milk residue is urged to flow from being adhered to the inner surface 15 of the funnel 13 and along the fluid passageway defined in the main body 12 to the milk collecting vessel 14. Therefore, residue milk is guided to the milk collecting vessel 14 and the loss of milk expressed from a user's breast will be minimized. The control unit 60 then stops the vibrating means 40 and the main body 12 and funnel 13 cease to vibrate.

In the present embodiment it is envisaged that the control unit 60 stops the vacuum pump unit 47 prior to operating the vibrating means 40. However, it will be appreciated that the control unit 60 may be operable to simultaneously operate the vacuum pump unit 47 and vibrating means 40.

In the present embodiment, the control unit 60 is operable to operate the vacuum pump unit 47 for a predetermined length of time before actuating the electric motor 42 to operate the vibrating means 40. Alternatively, the control unit 60 is operable to operate the vibrating means 40 in response to a signal from a sensor which detects the removal of a user's breast from the funnel 13. The vacuum pump unit 47 may also be configured to be stopped by a user operation, and the control unit 60 is then operable to operate the vibrating means 40 in response to a signal detecting stopping of the vacuum pump unit 47.

The control unit 60 is operable to operate the vibrating means 40 for a predetermined length of time.

Figure 9:
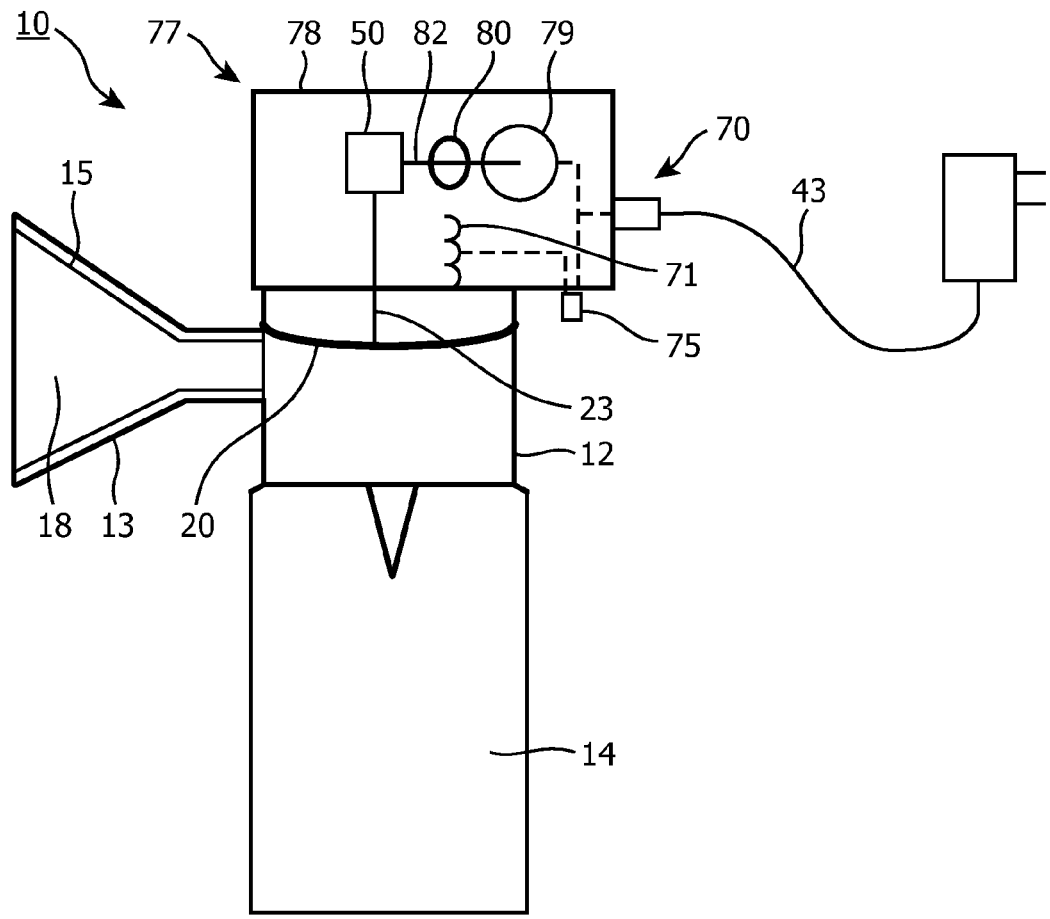
FIG. 9 shows a schematic cross-sectional of a breast pump according to a fifth embodiment.
Figure 10:
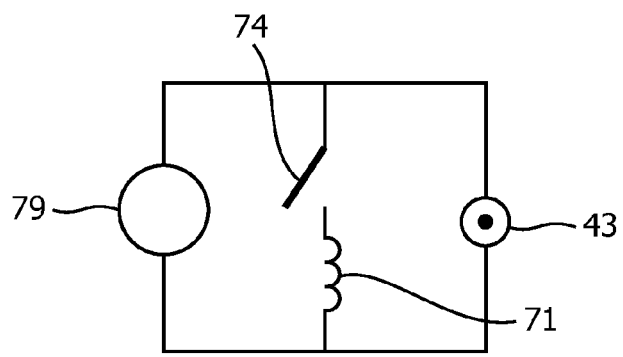
FIG. 10 shows an electrical diagram of the breast pump shown in FIG. 9.

Referring now to FIGS. 9 and 10, a fifth embodiment of a breast pump is shown. The breast pump shown in FIG. 9 has the same general arrangement and features as the breast pump shown in the third embodiment described above and shown in FIGS. 5 and 6, and so a detailed description will be omitted herein. Furthermore, features and components corresponding to features and components described above will retain the same reference numerals.

In FIG. 9, a vacuum pump unit 77 is shown comprising the diaphragm 20 disposed in the main body 12 to create a vacuum in the main body 12 and breast receiving recess 18 of the funnel 13 and a motor unit 78 mounted to the main body 12 which is connected to the diaphragm 20 by the connecting element 23, and cyclically deforms the diaphragm 20. The motor unit 78 comprises a pump motor 79 and a gearbox 50. The gearbox 50 and connecting member 23 form a mechanical link between the pump motor 79 and the diaphragm 20, so that the pump motor 79 is operable to cyclically deform the diaphragm 20. A power supply means 43 is connected to the pump motor 79 to supply power the pump motor 79. The power supply means 43 in the present embodiment is an external power supply unit which is connected to the pump motor 79 by a wire, although it will be appreciated that a battery may be used which is disposed in the motor unit 78.

Referring to FIG. 10, a vibrating means 70 is disposed in the motor unit 78. The vibrating means 70 comprises an electromagnet 71, a small permanent magnet 80 fixedly mounted to a rotating shaft 82 of the pump motor 79 and a switch 74. A push button 75, or other actuating means, is disposed on the motor unit 48 to actuate the switch 74 and activate the vibrating means 40. The electromagnet 71 is disposed proximate to the permanent magnet 80 fixedly mounted to the rotating shaft 82 of the pump motor 79 so that, when the electromagnet is energized due to activation of the switch 74, then the electromagnet acts on the permanent magnet 80 to successively draw the permanent magnet 80 toward, and urge the permanent magnet 80 away from, the electromagnet 71 so that the shaft of the pump motor 79 is unevenly balanced. Therefore, the vibrating means 70 induces the pump motor 79 to vibrate when the vibrating means is actuated.

Operation of the breast pump will now be described with reference to FIGS. 9 and 10. A user inserts a breast (not shown) into the breast receiving recess 18 formed by the funnel 13 and the vacuum pump unit 77 is then operated by supplying power to the pump motor 79 by the external power supply unit so that the diaphragm is cyclically deformed and milk is expressed from the user's nipple and flows from the breast receiving recess 18 along the fluid passageway defined by the main body 12 to the milk receiving vessel 14. The vibrating means 70 is not actuated such that the electromagnet 71 is not energized, and the pump motor 79 is therefore balanced and is not urged to vibrate. When the desired quantity of milk has been expressed, the user removes the breast pump 10 from the breast. However, milk residue is left on the inner surface 15 of the funnel 13 and along the fluid passageway defined in the main body 12.

The user then presses the push button 75 to actuate the vibrating means 70 and the electromagnet 71 is energized. The electromagnet then acts on the permanent magnet 80 to successively draw the permanent magnet 80 toward, and urge the permanent magnet 80 away from, the electromagnet 71 so that the shaft of the pump motor 79 is unevenly balanced and is induced to vibrate. The main body 12 and funnel 13 is therefore induced to vibrate and so milk residue is urged to flow from being adhered to the inner surface 15 of the funnel 13 and along the fluid passageway defined in the main body 12 to the milk collecting vessel 14. Therefore, residual milk is guided to the milk receiving vessel and the loss of milk expressed from a user's breast will be minimized. The user then releases the push button 75, which de-energizes the electromagnet 71, and the breast pump ceases to vibrate.

In the present embodiment it will be appreciated that the pump motor operates constantly, however the vibrating means 70 is operable to induce the shaft 82 to be unbalanced and therefore induce the breast pump to vibrate.

Although in the above described embodiment, the vibrating means 70 is operated by a switch 74, it will be appreciated that the breast pump may also comprise a control unit as described above in the fourth embodiment such that the control unit is configured to operate the vibrating means 70 and vacuum pump unit 77 of the present embodiment.

In the above embodiments a vacuum is generated in the breast receiving recess by a diaphragm being deformed due to a pump motor or manual action of a user. However, it will be appreciated that the vacuum pump unit may generate a vacuum in the breast receiving recess by other means, for example a constantly acting compressor driven by a pump motor with a pressure release valve to cyclically vary the air pressure. However, it will be appreciated that each of the means for inducing vibration in the main body and funnel described herein are applicable to such arrangements.

Figure 11:
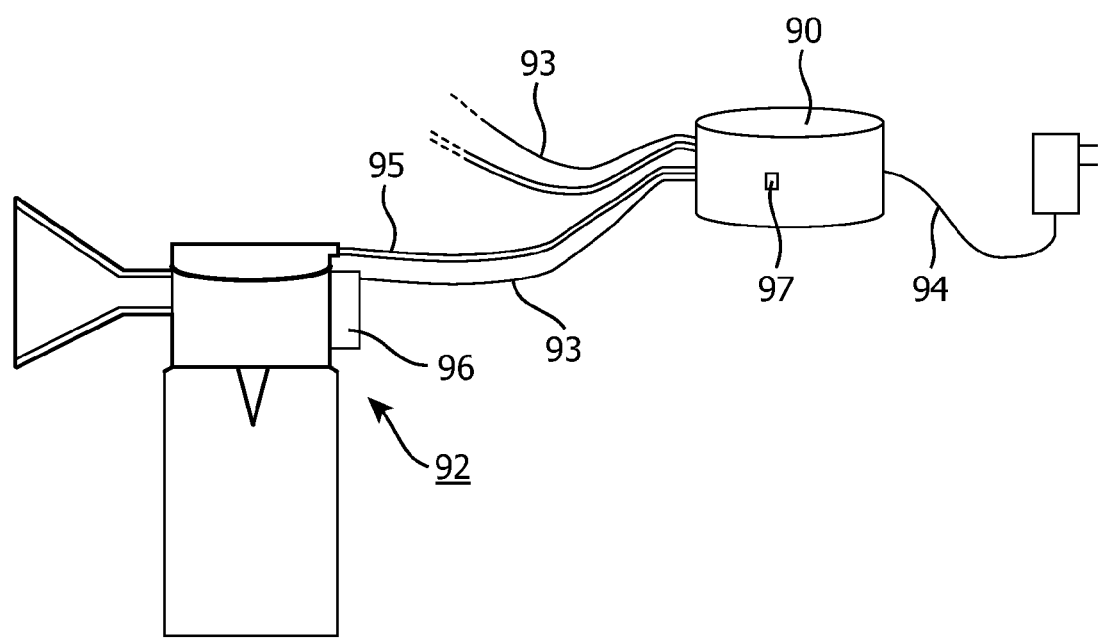
FIG. 11 shows a schematic cross-sectional of a breast pump according to a sixth embodiment.

Although in the above embodiments the vacuum pump unit and/or control means have been disposed on the vacuum pump body, it will be appreciated than in an alternative arrangement the or part of the vacuum pump unit may be disposed in a separate unit, for example a unit which is positioned on a desktop. In such an embodiment, two vacuum pump units may be connected to a central unit so that a user may extract milk from two breasts simultaneously. Such a breast pump assembly is shown in FIG. 11 and comprises a desktop unit 90, two breast pumps 92 (only a single breast pump is shown), connecting leads 93 and a power supply means 94. In the present embodiment the pump motor (not shown) is disposed in the desktop unit 90 and connector pipes 95 extend to each breast pump 92 to cyclically adjust the pressure in the main body of each breast pump 92. An unevenly balanced motor 96 is fixedly mounted to the main body of each breast pump 92, and the connecting leads 93 connect each unevenly balanced motor 96 to the desktop unit 90.

A button 97 is mounted on the desktop unit 90 to actuate a switch (not shown) and operate each unevenly balanced motor 96 to induce each breast pump 92 to vibrate.

Although in the above embodiments, a user's breast is disposed to abut against the inner surface 15 of the funnel and residual milk lies thereon, it will be appreciated that an insert (not shown) may be disposed in the breast receiving recess 18 of the funnel 13 in an attempt to improve a user's comfort and aid the expression of milk. In such an arrangement, it will be appreciated that an inner face of the insert (not shown) forms the inner surface 15 of the funnel 13 against which a user's breast is located, and on which residual milk expressed from a user's breast collects.

The invention has been described with reference to preferred embodiments only. Modifications and alterations to the embodiments falling within the scope of the appended claims are included within the scope of protection.

The invention claimed is:

1. A breast pump comprising a main body, a funnel, a vacuum pump unit to generate a vacuum and a vibrating means, wherein the vibrating means is configured to induce the main body and funnel to vibrate to promote the flow of residual milk on a surface of the funnel to flow to a milk collecting vessel, characterized in that the vibrating means is configured to vibrate following operation of the vacuum pump unit to express milk, wherein the vibrating means comprises an electrically driven vibrating element, the vacuum pump unit comprises a pump motor, and wherein the vibrating means comprises an electromagnet which is operable to act on a drive shaft of the pump motor to unbalance the pump motor when the electromagnet is operated so that the pump motor is induced to vibrate.

2. The breast pump of claim 1, wherein the vibrating means is actuated by a switch, and wherein the switch alternately actuates the vibrating means or the vacuum pump unit.

3. The breast pump of claim 1, further comprising a fluid passageway in the main body extending between the funnel and the milk collecting vessel.

4. The breast pump of claim 1, wherein a control unit is configured to operate the vibrating means after the vacuum pump unit has been operated for a predetermined length of time.

5. The breast pump of claim 1, wherein a control unit is configured to operate the vibrating means in response to a signal that the vacuum pump unit has stopped.

* * * * *